(12) United States Patent
Bailey et al.

(10) Patent No.: US 6,599,290 B2
(45) Date of Patent: Jul. 29, 2003

(54) ANTERIOR CERVICAL PLATING SYSTEM AND ASSOCIATED METHOD

(75) Inventors: Kirk J. Bailey, Blairstown, NJ (US); Rui J. Ferreira, Newark, NJ (US)

(73) Assignee: EBI, L.P., Parsippany, NJ (US)

( * ) Notice: Subject to any disclaimer, the term of this patent is extended or adjusted under 35 U.S.C. 154(b) by 0 days.

(21) Appl. No.: 09/836,722

(22) Filed: Apr. 17, 2001

(65) Prior Publication Data

US 2002/0151899 A1 Oct. 17, 2002

(51) Int. Cl.[7] ............................................. A61B 17/80
(52) U.S. Cl. ................................... 606/69; 606/104
(58) Field of Search ............................. 606/60, 69–71, 606/104, 61

(56) References Cited

U.S. PATENT DOCUMENTS

| | | | | |
|---|---|---|---|---|
| 2,248,054 A | * | 7/1941 | Becker | 81/457 |
| 2,580,821 A | | 1/1952 | Nicola | 128/92 |
| 2,780,223 A | | 2/1957 | Haggland | 128/92 |
| 3,741,205 A | | 6/1973 | Markolf et al. | 128/92 |
| 4,388,921 A | * | 6/1983 | Sutter et al. | 606/71 |
| 4,473,068 A | | 9/1984 | Oh | 128/92 |
| 4,484,570 A | | 11/1984 | Sutter et al. | 128/92 |
| 5,053,036 A | | 10/1991 | Perren et al. | 606/69 |
| 5,057,109 A | | 10/1991 | Olerud | 606/61 |
| 5,129,903 A | | 7/1992 | Luhr et al. | 606/71 |
| 5,139,498 A | | 8/1992 | Astudillo Ley | 606/69 |
| 5,147,360 A | | 9/1992 | Dubousset | 606/61 |
| 5,180,381 A | | 1/1993 | Aust et al. | 606/61 |
| 5,346,492 A | | 9/1994 | Morgan | 606/60 |
| 5,364,399 A | | 11/1994 | Lowery et al. | 609/69 |
| 5,423,826 A | | 6/1995 | Coates et al. | 606/96 |
| 5,468,242 A | | 11/1995 | Reisburg | 606/69 |
| 5,520,690 A | | 5/1996 | Errico et al. | 606/61 |
| 5,578,034 A | | 11/1996 | Estes | 606/61 |
| 5,676,666 A | | 10/1997 | Oxland et al. | 606/61 |
| 5,681,311 A | | 10/1997 | Foley et al. | 606/61 |
| 5,690,631 A | | 11/1997 | Duncan et al. | 606/69 |
| 5,704,936 A | | 1/1998 | Mazei | 606/61 |
| 5,707,372 A | | 1/1998 | Errico et al. | 606/61 |
| 5,713,900 A | | 2/1998 | Benzel et al. | 606/61 |
| 5,735,853 A | * | 4/1998 | Olerud | 606/71 |
| 5,766,176 A | | 6/1998 | Duncan | 606/69 |
| 5,800,433 A | | 9/1998 | Benzel et al. | 606/61 |
| 5,814,048 A | | 9/1998 | Morgan | 606/69 |
| 5,843,082 A | | 12/1998 | Yuan et al. | 606/61 |
| 5,876,402 A | | 3/1999 | Errico et al. | 606/61 |
| 5,904,683 A | | 5/1999 | Pohndorf et al. | 606/61 |
| 5,954,722 A | | 9/1999 | Bono | 606/61 |
| 5,980,540 A | | 11/1999 | Bruce | 606/151 |
| 6,036,693 A | | 3/2000 | Yuan et al. | 606/61 |
| 6,039,740 A | | 3/2000 | Olerud | 606/72 |
| 6,090,111 A | | 7/2000 | Nichols | 606/61 |
| 6,117,173 A | | 9/2000 | Taddia et al. | 623/16.11 |
| 6,152,927 A | | 11/2000 | Farris et al. | 606/69 |
| 6,193,721 B1 | | 2/2001 | Michelson | 606/70 |
| 6,228,085 B1 | | 5/2001 | Theken et al. | 606/61 |
| 6,235,033 B1 | | 5/2001 | Brace et al. | 606/69 |

(List continued on next page.)

*Primary Examiner*—Kevin Shaver
*Assistant Examiner*—Michael B. Priddy
(74) *Attorney, Agent, or Firm*—Harness, Dickey & Pierce, PLC (57) ABSTRACT

An anterior cervical plating system for securing multiple bone segments relative to each other includes a plate member having multiple pairs of nodes. Each node defines a bone screw aperture. Linking segments connect the pairs of nodes to one another. Between adjacent linking segments are elongated viewing windows. The bone screw apertures each include an integral locking mechanism to ensure that the bone screws do not back out of the plate member. The locking mechanisms and the bone screw apertures allow for angular freedom of insertion of the bone screws into a vertebral body or other bone portion.

21 Claims, 5 Drawing Sheets

U.S. PATENT DOCUMENTS

| | | |
|---|---|---|
| 6,261,291 B1 | 7/2001 | Talaber et al. ................. 606/69 |
| 6,273,899 B1 * | 8/2001 | Kramer ....................... 606/194 |
| D449,692 S | 10/2001 | Michelson |
| 6,331,179 B1 | 12/2001 | Freid et al. .................... 606/61 |
| 6,361,537 B1 | 3/2002 | Anderson .................... 606/69 |
| 6,383,186 B1 | 5/2002 | Michelson ................... 606/69 |
| 6,398,783 B1 | 6/2002 | Michelson ................... 606/70 |
| 6,402,756 B1 | 6/2002 | Ralph et al. .................. 606/71 |
| 6,402,759 B1 * | 6/2002 | Strong et al. ............... 606/104 |
| 6,413,259 B1 | 7/2002 | Lyons et al. .................. 606/69 |
| 6,416,528 B1 | 7/2002 | Michelson .................. 606/185 |
| 6,423,068 B1 * | 7/2002 | Reisberg et al. .............. 606/69 |
| 6,428,542 B1 | 8/2002 | Michelson ................... 606/70 |
| 2002/0045896 A1 | 4/2002 | Michelson ................... 606/61 |
| 2002/0077630 A1 | 6/2002 | Lin .............................. 606/69 |
| 2002/0120268 A1 | 8/2002 | Berger ......................... 606/61 |
| 2002/0120273 A1 | 8/2002 | Needham et al. ............. 606/61 |

* cited by examiner

ANTERIOR CERVICAL PLATING SYSTEM AND ASSOCIATED METHOD

FIELD OF THE INVENTION

The present invention relates generally to orthopedic surgical procedures, most particularly for use in fixation of the spine. More particularly, the present invention relates to a system for anteriorly fixating the cervical spine. The present invention also pertains to a related method of withdrawing a bone screw from a plate.

BACKGROUND OF THE INVENTION

In certain orthopedic surgical procedures, it is necessary to secure multiple bones or bone portions relative to each other. For example, in spinal surgeries, the fusion of two or more vertebrae bodies is required to secure a portion of the spinal column in a desired position. This need may be the result of physical trauma from fractures or dislocations, degenerative diseases, or tumors.

One such spinal fixation procedure involves the attachment of a prosthesis or plate to the anterior side of the cervical portion of the spine. The procedure requires anteriorly accessing the spine and securing a prosthetic plate to the one or more cervical vertebrae. This allows fusion of the one or more cervical vertebrae in a particular orientation so to facilitate healing or to repair a condition of the patient.

Various fusion plates and plating systems are known for anteriorly fusing the cervical spine. While known anterior plating systems have addressed certain requirements associated with the surgical repair of bone, in general, and spinal fusion, particularly, all are associated with limitations. The requirements associated with spinal stability and system reliability over an extended period of use often conflict with the requirements of an easy to use implant. For example, strength requirements for a fusion plate tend to make the plate bulky and adversely effect intra-operative and postoperative viewing of the associate area of the spine. In this regard, the affected region of the cervical spine cannot be easily viewed using MRI or x-ray procedures to verify that the desired fusion of the cervical spine is complete and/or that the alignment of the cervical vertebrae is proper.

Additionally, ensuring that bone screws do not loosen over time or back out from the plate tends to complicate implantation of known anterior plating systems. Known locking mechanisms generally ensure that the bone screws placed into the vertebrae through the plating system do not loosen or back out from the plate. When a locking mechanism has been included with known anterior cervical plating systems, it generally incorporates a discrete fastener or other element. As such, an additional surgical step is required. Furthermore, known locking mechanisms do not adequately permit the removal of an associated bone screw when required.

Furthermore, known plating systems often do not permit sufficient angular freedom for bone screws relative to a plate. Generally, known plating systems have defined bores through which bone screws are placed at a predefined angle. Therefore, the operating surgeon often does not have freedom to insert the bone screws into the vertebrae as to best fit the anatomy of the individual patient. While some known systems do permit bone screw angulation, they typically are not adapted to be used with an easy to use locking mechanism.

It remains desirable in the pertinent art to provide an anterior cervical plating system that addresses the limitations associated with known systems, including but not limited to those limitations discussed above.

SUMMARY OF THE INVENTION

The present invention relates to plating systems for the fixation of the cervical spine. In particular, the present invention relates to an anteriorly placed plating system for a cervical portion of the spine. According to one aspect, the present invention relates to a locking mechanism for preventing the withdrawal of locking bone screws from a plate after being implanted. The locking mechanism is integral to the plating system and does not require the additional insertion of additional fasteners or other discrete members into the plate after the bone screws have been fastened to the spine. The locking mechanism preferably allows for angular freedom of the bone screws as they are inserted through the plate.

In another aspect, the present invention relates to a plate member of a cervical plating system that permits enhanced viewing of an adjacent portion of the spine area intra-operatively and post-operatively. the plate member includes a first pair of nodes having a first node and a second node defining first and second bone screw apertures, respectively. The first and second nodes are at least partially circular in shape and spaced apart from one another in a first direction. The plate member additionally includes a second pair of nodes having a third node and a fourth node defining third and fourth bone screw apertures, respectively. The third and fourth nodes are at least partially circular in shape and spaced apart from one another in the first direction. The plate member further includes a first plurality of linking segments extending in a second direction substantially perpendicular to the first direction and connecting the first and second pairs of nodes. Adjacent linking segments define elongated viewing windows.

In a further aspect, the present invention relates to a method of surgically repairing bone with an elongated plate having a plurality of bone screw apertures. The method includes the step of locating a locking ring in one of the bone screw apertures. The locking ring defines a locking ring opening and is resiliently expandable from a retracted state to an expanded state such that the locking ring opening has a first opening diameter in the retracted state and a second, larger diameter in the expanded state. The method additionally includes the step of removing the bone screw from the one bone screw aperture with a tool having a first portion engaging the head of the bone screw and a second portion resiliently expanding the locking ring to the expanded state.

In yet another aspect, the present invention relates to a system for surgically repairing bone. The system includes an elongated plate having a plurality of bone screw apertures. A locking ring is disposed in one of the bone screw apertures. The locking ring defines a locking ring opening and is resiliently expandable from a retracted state to an expanded state such that the locking ring opening has a first opening diameter in the retracted state and a second, larger diameter in the expanded state. A bone screw is inserted into the one of the bone screw apertures. The bone screw has a head with a diameter greater than the first opening diameter and less than the second opening diameter. The system further includes a tool for removing the bone screw from the one bone screw aperture. The tool has a first portion engaging the head of the bone screw and a second portion for resiliently expanding the locking ring to the expanded state.

An advantage of the present invention is to provide an anterior cervical plating system that provides a locking mechanism including a pre-attached locking ring, thereby eliminating the need for discrete locking components.

Another advantage of the present invention is to provide an anterior cervical plating system with an integral locking mechanism that maintains a low profile and thereby minimizes interferences with anatomical soft tissue structure.

Another advantage of the present invention is to provide an anterior cervical plating system that provides a plate having an open design permitting intra-operative visualization of bone grafts and vertebrae end plates, as well as post-operative visualization of bone graft consolidation and spinal orientation on an anterior/posterior x-ray.

Another advantage of the present invention is to provide an anterior cervical plating system that provides a variable angle bone screw permitting approximately 20° of screw angulation.

Another advantage of the present invention is to provide a cervical plating system including a predefined angle. Therefore, the plate need not be manually fashioned to fit the spine thereby decreasing surgical time and interference with soft tissue after implantation.

Additional advantages and further areas of applicability of the present invention will become apparent from the following detailed description and appended claims. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

The following description of the preferred embodiment of the present invention will be understood to be merely exemplary in nature and in no way is intended to limit the subject invention, its application, or uses.

Figure 1:
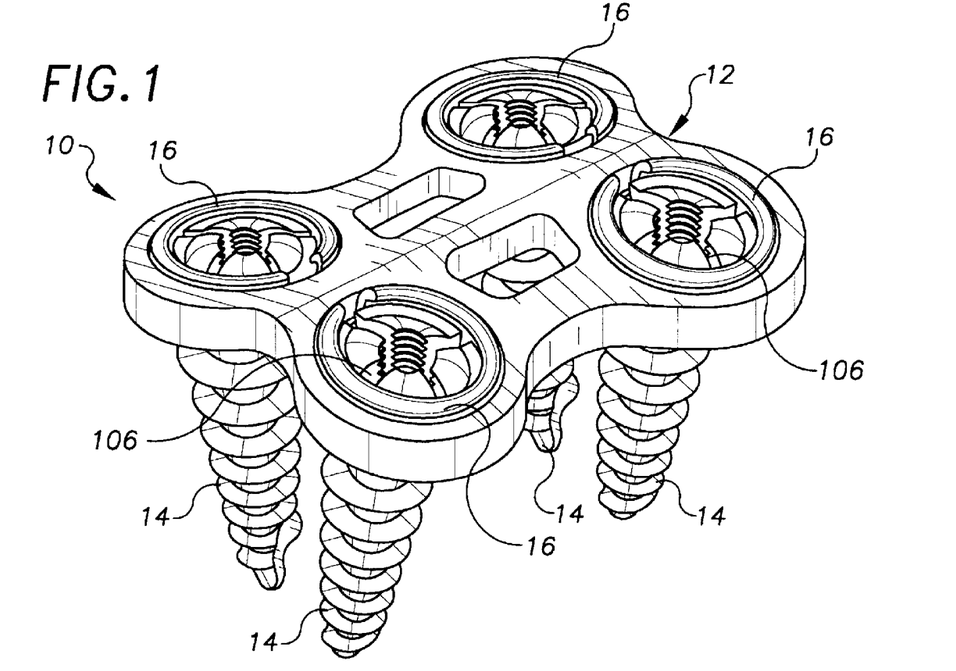
FIG. 1 is a perspective view of an anterior cervical plating system according to the teachings of a preferred embodiment of the present invention, the system illustrated to include a first plate member.

With initial reference to FIG. 1, a plating system according to the teachings of a preferred embodiment of the present invention is illustrated and generally identified at reference number 10. The embodiment illustrated is specifically intended for use as an anterior cervical plating system. However, it will become apparent to those skilled in the art below that the teachings of the present invention are suitable for other applications in which surgical repair of bone with a plate is desired.

Figure 2:
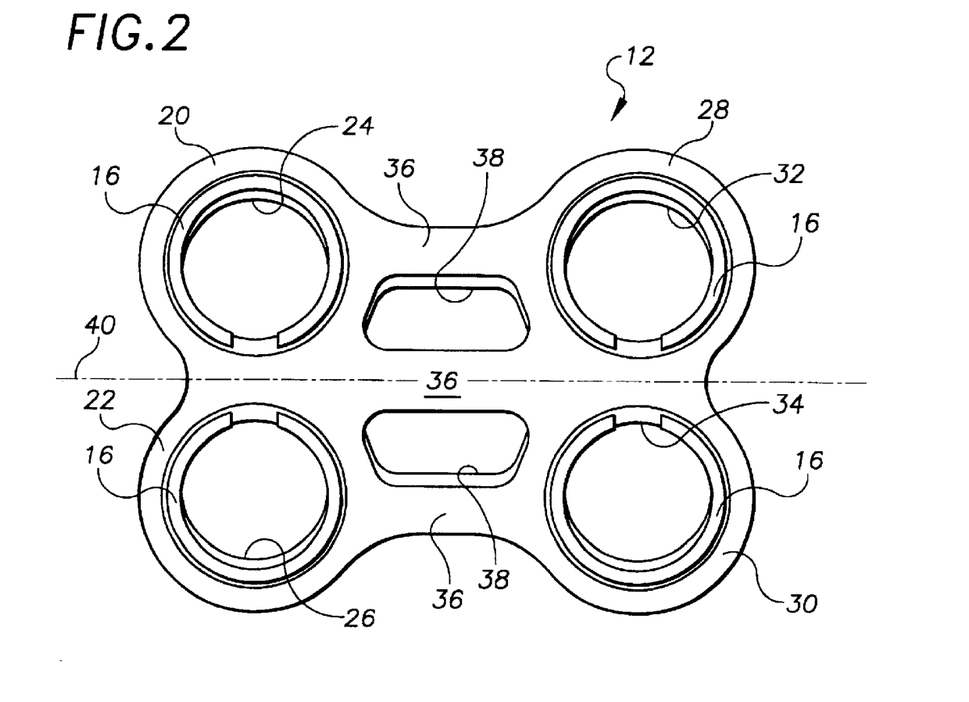
FIG. 2 is a top view of the first plate member of the anterior cervical plating system according to the present invention.
Figure 3:
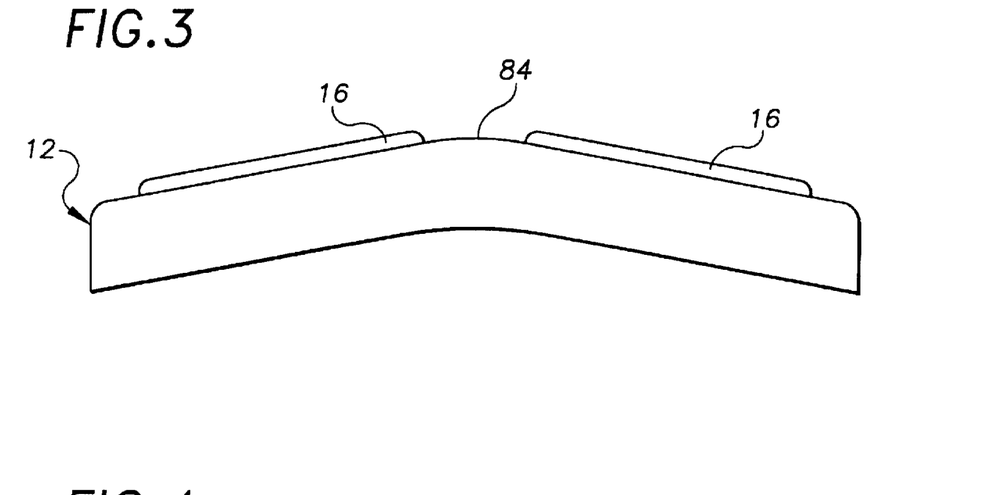
FIG. 3 is an end view of the first plate member of the anterior cervical plating system according to the present invention.
Figure 4:
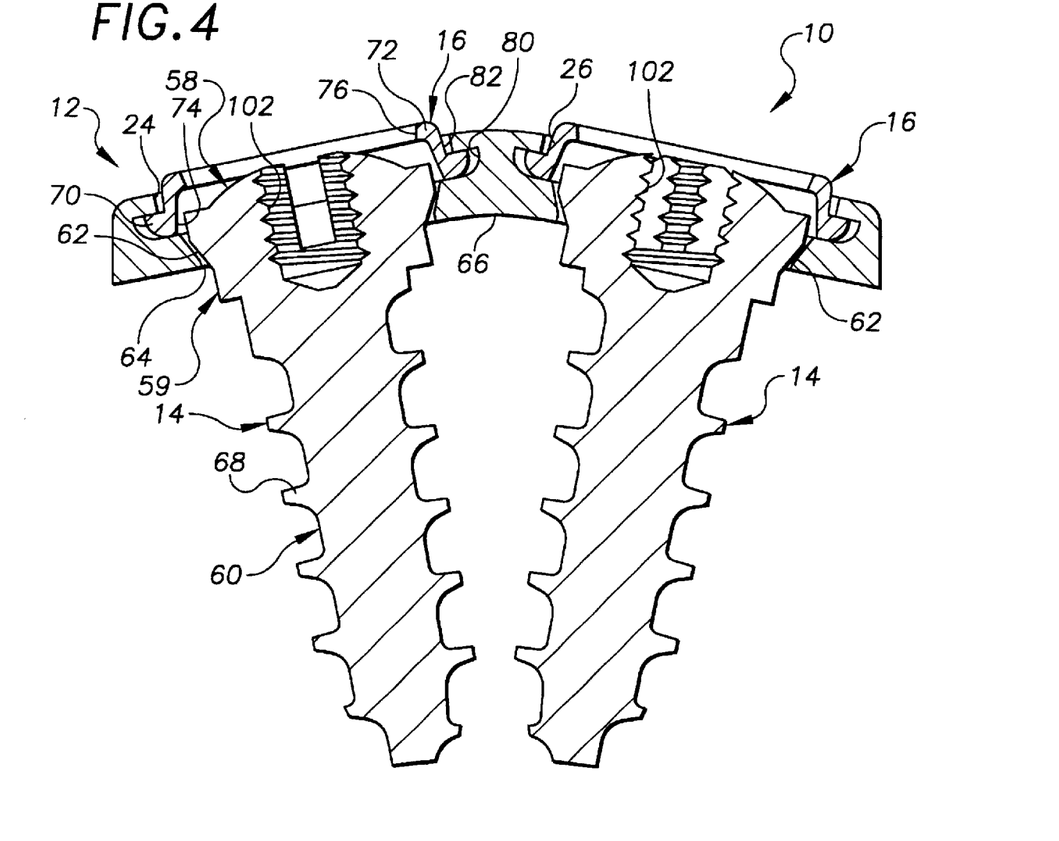
FIG. 4 is a cross-sectional end view of the plating system according to the teachings of a preferred embodiment of the present invention.

With continued reference to FIG. 1 and additional reference to FIGS. 2–4, the anterior plating system 10 according to the preferred embodiment of the present invention is shown to generally include a first plate member 12. The first plate member 12 is intended to address one disk level and attach to two adjacent vertebrae. The anterior plating system 10 is further shown to generally include a plurality of bone screws or fasteners 14 and a plurality of locking mechanisms 16 for preventing the bone screws 14 from backing out of the plate member 12 or loosening with respect to a vertebral body 18 (shown in FIG. 6) or other bone portion.

The plate member 12 includes a first pair of nodes having a first node 20 and a second node 22. The first and second nodes 20 and 22 define first and second bone screw apertures 24 and 26, respectively. The first and second nodes 20 and 22 are generally cylindrical in shape and are laterally spaced apart from one another in a first direction. In the embodiment illustrated and in a manner to be more fully discussed below, the first and second bone screw apertures 24 and 26 are intended to receive a pair of fasteners 14 for engaging a first vertebral body 18.

In a similar manner, the plate member 12 includes a second pair of nodes having a third node 28 and a fourth node 30. The third and fourth nodes 28 and 30 define third and fourth screw apertures 32 and 34, respectively. Again, the third and fourth nodes 28 and 30 are generally cylindrical in shape and spaced apart from one another in a lateral direction. The third and fourth bone screw apertures 32 and 34 are intended to receive a pair of fasteners 14 for engaging a second vertebral body 18.

The plate member 12 is further shown to include a plurality of axial bridges or linking segments 36 which connect the first and second pairs of nodes. The linking segments of the first plurality of linking segments 36 extend in a longitudinal or axial direction which is essentially perpendicular to the lateral direction in which the nodes of the pairs of nodes are spaced apart. The first plurality of linking segments 36 define elongated viewing windows. Explaining further, the elongated viewing windows 38 contribute to an open design of the plate member 12 that permits intra-operative visualization of bone grafts and vertebrae end bodies, as well as post-operative visualization of bone graft consolidation and spinal orientation on an anterior/posterior x-ray.

In the embodiment illustrated, the plate member 12 is illustrated to include three (3) linking segments 36. As such, adjacent linking segments 36 define two (2) elongated viewing windows 38. Those skilled in the art will readily appreciate that the particular number of linking segments 36 and elongated viewing windows 38 may be altered within the scope of the present invention.

As particularly shown in the end view of FIG. 3 and the cross-sectional view of FIG. 4, the plate member 12 is contoured about a longitudinally extending midline 40 (shown in FIG. 2). In this regard, the plate member 12 is shown to include a first lateral half oriented at an obtuse angle relative to a second lateral half. In one application, the obtuse angle is between approximately 160° and 170°. The contour of the plate member eliminates manual fashioning of the plate member 12 to fit the contour of the spine, thereby decreasing surgical time. The contour of the plate member 12 also decreases interference with adjacent soft tissue after implantation.

Figure 5:
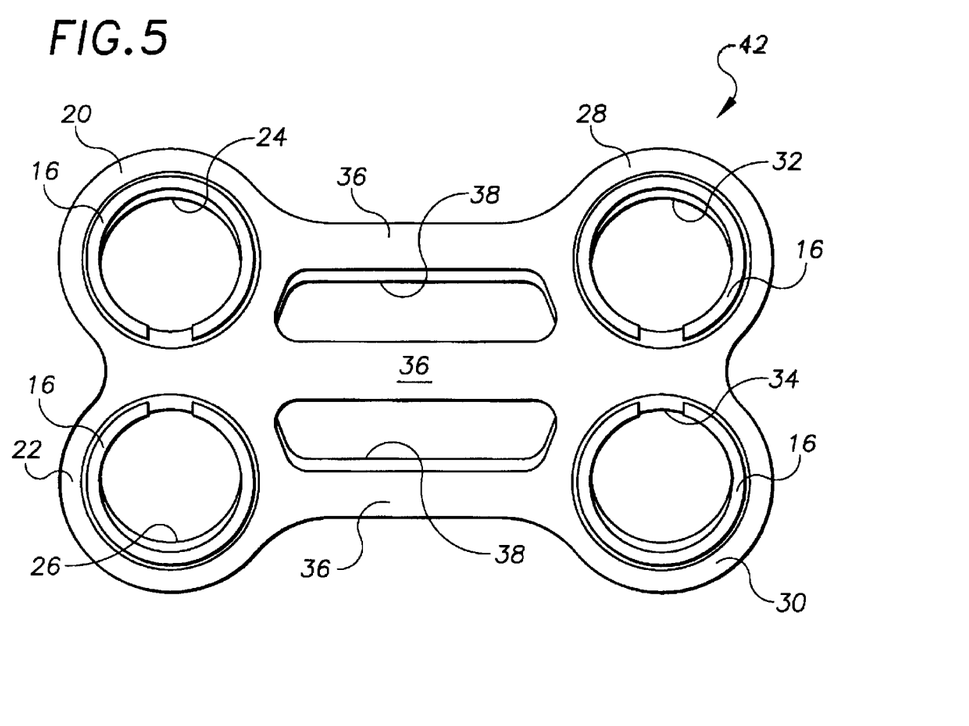
FIG. 5 is a top view of a second plate member of the anterior cervical plating system according to the present invention.

With reference to FIG. 5, a second plate member 42 of the anterior cervical plating system 10 of the present invention is illustrated. The second plate member 42 shares various features with the first plate member 12. For this reason, like reference numerals have been used to identify substantially identical elements between the first and second plate members 12 and 42. The second plate member 42 differs from the first plate member 12 in that the linking segments 36 are longer and the viewing windows 38 are correspondingly longer. The second plate member 42 is intended to illustrate the flexibility of the present invention to accommodate patients having variable spinal dimensions. It will be understood that the length of the linking segments 36 may be longer or shorter than the linking segments 36 of plate members 12 and 42.

Figure 6:
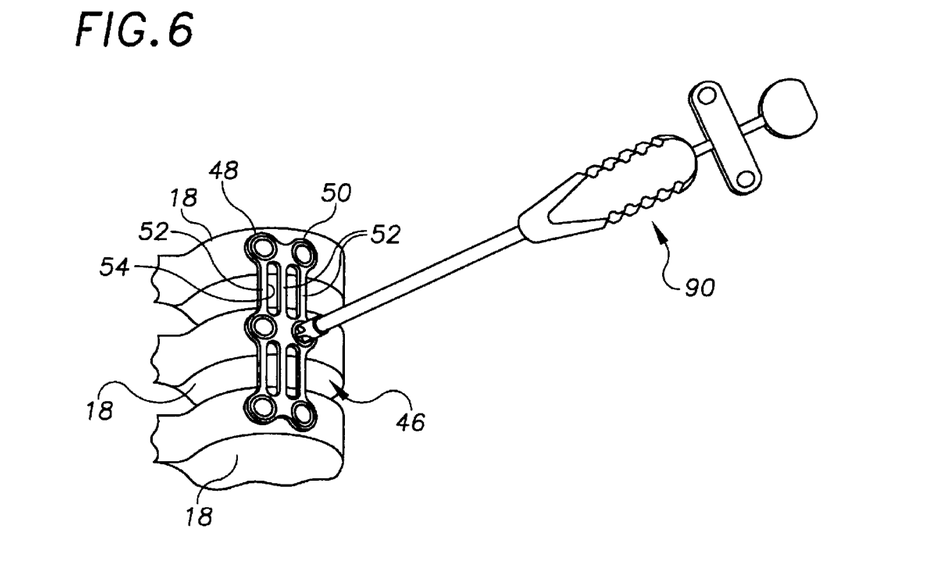
FIG. 6 is a perspective view of a third plate member of the anterior cervical plating system according the present invention, the third plate member shown secured to a cervical portion of a spine and further shown operatively associated with a tool for inserting and removing the bone screws.

With reference to FIG. 6, a third plate member 46 of the anterior cervical plating system 10 of the present invention is illustrated. The third plate member or two disk level plate member 46 is intended to address two disk levels by attachment to three adjacent vertebrae. The third plate member 46 is similar to the second plate member 42 and additionally incorporates a third pair of nodes. The third pair of nodes has fifth and sixth nodes 48 and 50 defining fifth and sixth bone screw apertures (not specifically shown). As discussed with respect to the nodes described above, the fifth and sixth nodes 48 and 50 are generally cylindrical in shape and spaced apart from one another in the lateral direction. The bone screw apertures of the fifth and sixth nodes 48 and 50 receive bone screws 14 for engaging a third vertebral body 18 or other bone portion.

The third pair of nodes is connected to the second pair of nodes through a second plurality of linking segments 52. The second plurality of linking segments extend in the axial or longitudinal direction. Again, adjacent linking segments 52 of the second plurality of linking segments define elongated viewing windows 54.

The bone screws 14 of the system 10 of the present invention will be understood to be identical. As will become apparent below, in the exemplary embodiment the bone screws 14 cooperate with the plate member 12 to provide a range of angular freedom of the bone screws 14 relative to the plate 12. Alternatively, the bone screws 14 and apertures of the plate member 12 can be constructed in a known manner to restrict or prevent such angular freedom. In the embodiment illustrated, the bone screws 14 are permitted to articulate universally relative to the plate member 12 through a range of approximately 20°. Such relative articulation allows for operative freedom in obtaining purchase of the bone screw in the vertebral bodies 18. As shown most clearly in the cross-sectional view of FIG. 4, the bone screws 14 adjacent to one another about the longitudinally extending center line 40 of the plate member 12 preferably converge as they extend into the vertebral body 18.

Each of the bone screws 14 is illustrated to include a head portion 58, a neck portion 59 and a shaft portion 60. The head portion 58 is shown to include a partially spherical segment 62 that engages an inwardly tapering lower portion 64 of the bone screw aperture 24, for example. These cooperating surfaces 62 and 64 facilitate relative movement between the bone screw 14 and associated one of the apertures of the plate member 12. The diameter of the head portion 58 of the bone screw 14 is larger than the opening of the bone screw aperture at a lower surface 66 of the plate member 12, thereby preventing the bone screw 14 from passing completely through the bone screw aperture.

The shaft 60 is shown to have a tapered shape with a relatively high pitch thread 68. The specific shaft features such as thread pitch, shaft diameter, and the like, are a matter of design choice and surgical preference.

In the exemplary embodiment illustrated, a locking mechanism in the form of a locking ring 16 is disposed within each of the bone screw apertures. The locking rings are illustrated as split locking rings 16 and are retained within the bone screw apertures. As such, discrete fasteners or other locking mechanisms are eliminated.

Each of the locking rings 16 is shown to include a first or lower radially extending flange 70 and a second or upper radially extending flange 72. The first radially extending flange 70 defines a lower opening 74 and the second radially extending flange 72 defines an upper opening 76. The first radially extending flange 70 is retained within an annular groove 80 formed in the sidewall of each of the bone screw apertures. The first and second radially extending flanges 70 and 72 are connected by an intermediate segment 82 such that the second radially extending flange is positioned slightly above an upper surface 84 of the plate member 12.

Figure 10:
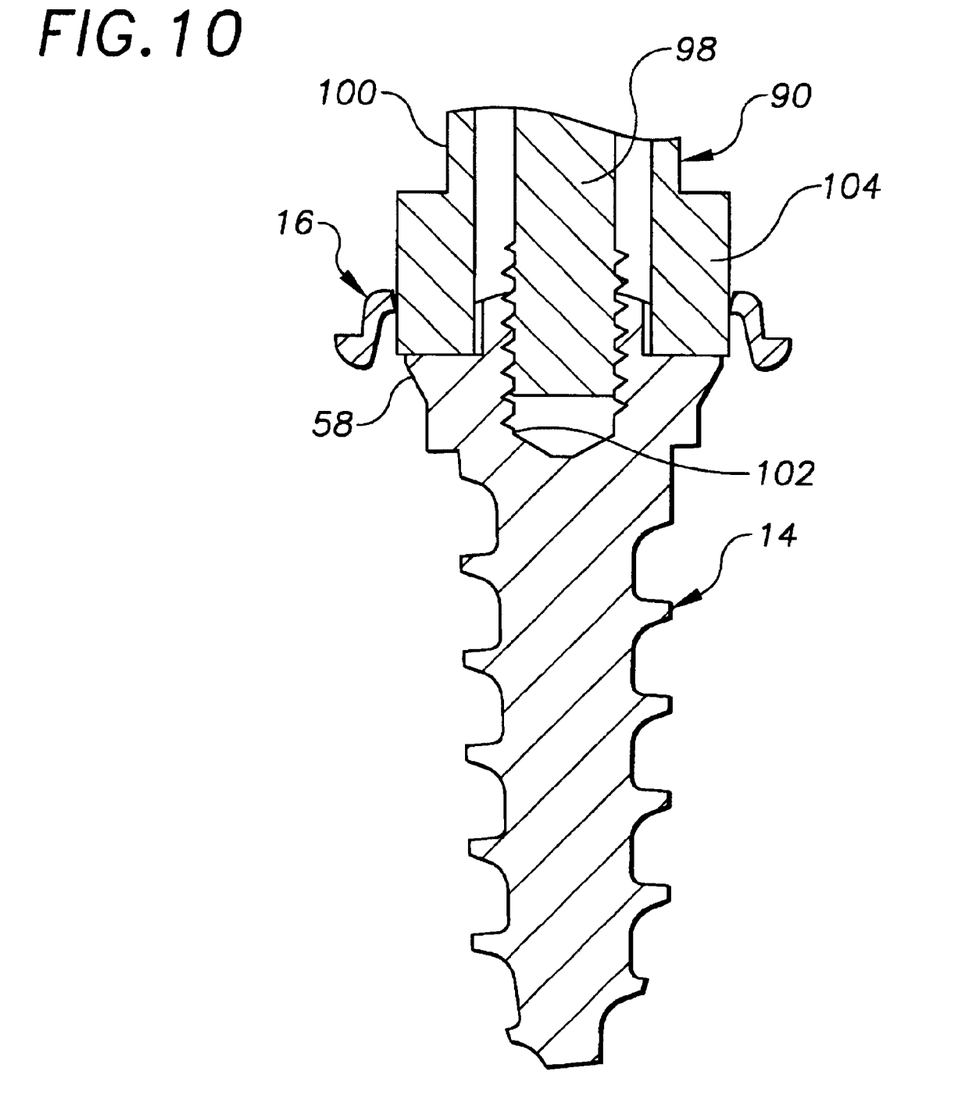
FIG. 10 is a cross-sectional view illustrating engagement of the tool with one of the bone screws shown operatively associated with a locking ring.

Each of the locking rings 16 is constructed of a suitable metal and is resiliently expandable from a retracted state to an expanded state. The retracted state is shown in FIGS. 1–4. The expanded state is shown in FIG. 10. When the locking ring 16 is in its retracted state, the opening 76 of the second radially extending flange 72 has a first diameter that is smaller than the diameter of the head portion 58. When the locking ring is in the expanded state, the diameter of the opening 76 is slightly greater than the diameter of the head portion 58 to thereby allow the head portion 58 to pass through the opening 76.

The bone screws 14 can be inserted with a conventional tool (not shown) having a philips-type head. When the bone screws 14 engage a vertebral body 18 and through rotation are drawn downward, the spherical segment 62 of the head portion 58 resiliently expands the locking member 16 from the retracted state to the expanded state. After the head portion 58 passes completely through the opening 76, the locking ring 16 resiliently returns to its retracted state and provides an audibly perceivable click. In this manner, the bone screws 14 are prevented from backing out relative to the plate member 12 and from loosening their purchase within the vertebral bodies 18. The particular configuration of the locking member 16 effectively prevents backing out of the bone screws 14. In this regard, if a bone screw 14 begins to back out, the head 58 of the bone screw 14 will engage a conically tapered inner surface of the locking ring 16. Such engagement forces the first radially extending flange 70 radially outward into the groove 80.

Turning now to FIGS. 6–10, a tool 90 for removing the bone screws 14 is illustrated. The tool 90 may also be used to insert the bone screws 14. However, the conventional philips-type screwdriver may provide the surgeon with better visibility of the head 58.

Figure 7:
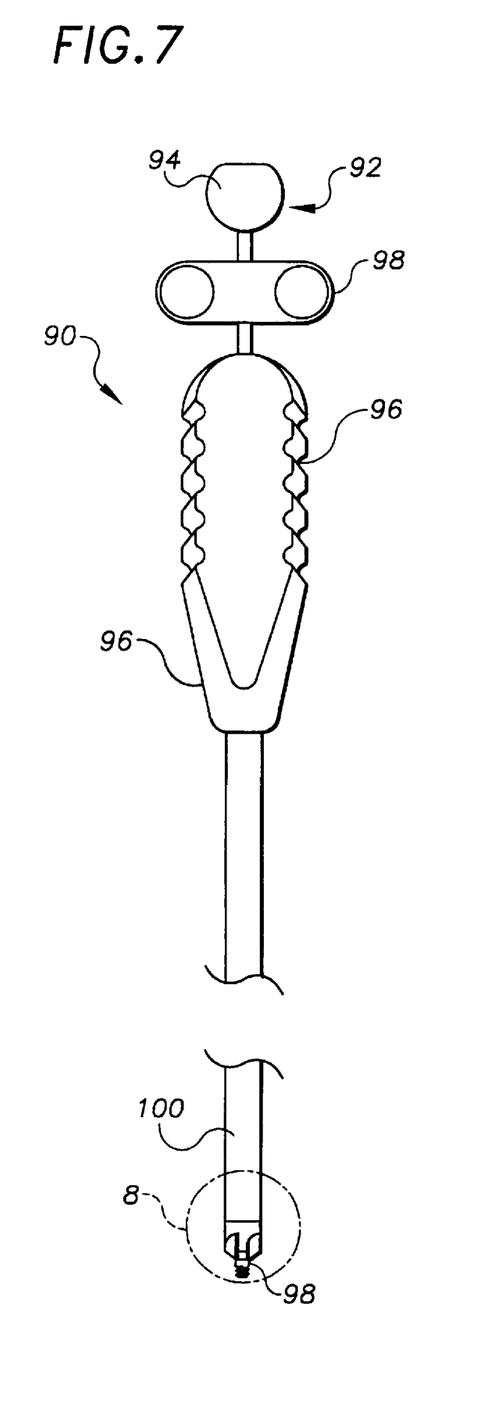
FIG. 7 is an enlarged side view of the tool shown in FIG. 6.
Figure 8:
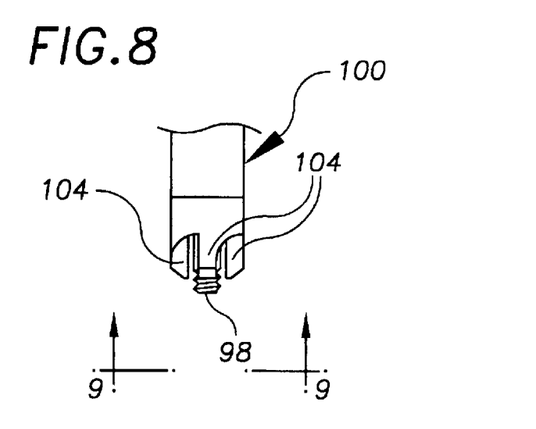
FIG. 8 is an enlarged view illustrating the details shown in circle 8 identified in FIG. 7.
Figure 9:
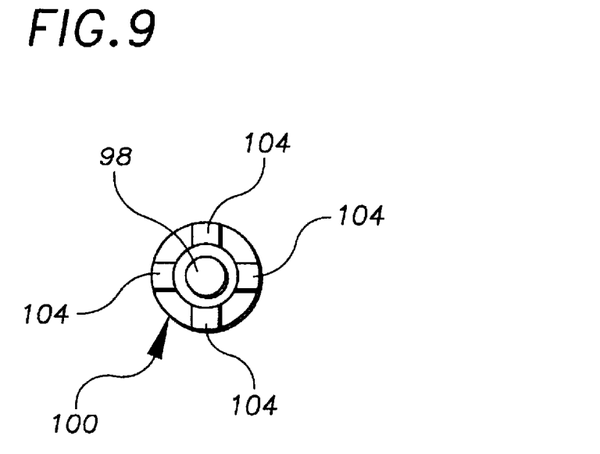
FIG. 9 is an enlarged end view of the tool taken in the direction of arrow 9 shown in FIG. 8.

The tool 90 is illustrated to include a handle portion 92 having an upper portion or knob 94, a lower portion 96, and an intermediate portion 97. The upper portion 94 is adapted to rotate with a first portion or first drive portion 98, while the lower portion 96 is adapted to rotate with a second portion or second drive portion 100.

The intermediate portion 98 translates the first drive portion 97 relative to the second drive portion 100. The first drive portion 98 is illustrated as an externally threaded shaft and is adapted to engage an internally threaded aperture 102 of the head portion 58 of each of the bone screws 14. The second drive portion 100 comprises a hollow cylindrical member surrounding the first portion 98 and includes a tip having four drive elements 104 equally spaced about the first drive member 98. The drive elements 104 are adapted to engage a corresponding number of slots 106 (shown in FIG. 1) equally spaced about the head portion 58 of each of the bone screws 14. The drive elements 104 include outer surfaces lying on a circle having a diameter substantially equal to the diameter of the opening 76 when the locking ring 16 is in the expanded state. The diameter of the circle is slightly greater than the diameter of the head portion 58.

When the bone screws 14 are implanted into the vertebral bodies 18 (in the orientation shown in FIG. 4, for example), the tool 90 can be used to retract the bone screws 14. The first portion 98 threadably engages the internally threaded aperture 102 of the head portion 58 through rotation of the upper portion 94 of the handle 92 in a clockwise direction. Rotation of the intermediate portion 97 of the handle 92 draws the tool 90 down onto the implanted bone screw 14. As the second portion 100 is drawn downward, the drive elements 104 resiliently expand the locking member 16 from its retracted state to its expanded state and the drive elements 104 engage the slots 106 of the head portion 58. Once the locking ring 16 expands, the lower portion 96 of the handle 92 can be rotated to correspondingly rotate the second drive portion 100 and back the bone screw 14 out of the associated bone screw aperture.

In one application, the preferred material of the plate and the bone screws of the present invention is a titanium alloy. One suitable alloy is Ti-6Al-4V. However, it will be understood that the preferred material is not the only material form which the components of the presently disclosed invention may be formed. In this regard, the plate and bone screws may be constructed of any suitable biocompatible material which has the structural strength and durability to withstand the cyclical loading associated with long term fixation.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. For example, additional pairs of nodes may be incorporated for addressing additional disk levels. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed:

1. A spinal plating system comprising;
    an elongated plate having a plurality of bone screw apertures;
    a locking ring disposed in one of the bone screw apertures, the locking ring having at least a portion resiliently expandable from a retracted state to an expanded state;
    a bone screw inserted into the one of the bone screw apertures, the bone screw having a head with a diameter sized such that in the retracted state the locking ring prevents the bone screw from backing out of the plate and in the expanded state the locking ring permits insertion and removal of the bone screw relative to the one bone screw aperture; and
    a tool for removing the bone screw from the one bone screw aperture, the tool having a first portion coupled to the head of the bone screw and a second portion resiliently expanding the locking ring to the expanded state.

2. The spinal plating system of claim 1, wherein the first portion is threadably engaged with the head of the bone screw.

3. A plating system for securing a first portion of bone to a second portion of bone, the plating system comprising:
    a plate member defining a plurality of bone screw apertures, at least one of the plurality of bone screw apertures including an annular groove formed in a sidewall portion;
    a plurality of bone screws each inserted into an associated bone screw aperture of the plurality of bone screw apertures; and
    a locking ring retained in at least one of the plurality of bone screw apertures and operative to prevent backing out of the bone screw inserted in the at least one bone screw aperture, the locking ring including a first radially extending flange disposed in the annular groove of the at least one bone screw aperture and a second radially extending flange upwardly spaced from the first radially extending flange; the locking ring being resiliently expandable from a retracted state to an expanded state to permit insertion of one of the bone screws into the at least one bone screw aperture;
    wherein each bone screw of the plurality of bone screws has a head having a head diameter and further wherein the second radially extending flange defines an upper opening having a first diameter when the locking ring is in the retracted state and a second diameter when the locking ring is in the expanded state, the first diameter being less than the head diameter, the second diameter being greater than the head diameter.

4. The plating system for securing a first portion of bone to a second portion of bone of claim 3, wherein the first radially extending flange defines a lower opening having a third diameter when the locking ring is in the retracted state, the third diameter being greater than the head diameter.

5. The plating system for securing a first portion of bone to a second portion of bone of claim 3, wherein the plurality of bone screws and the plurality of bone screw apertures cooperate to permit universal movement of each of the bone screws relative to the associated bone screw aperture.

6. The plating system for securing a first portion of bone to a second portion of bone of claim 5, wherein a head of each of the bone screws includes a partially spherical portion for articulably engaging the plate member.

7. The plating system for securing a first portion of bone to a second portion of bone of claim 3, wherein the locking ring is a split locking ring.

8. The plating system for securing a first portion of bone to a second portion of bone of claim 3, wherein one of the plurality of bone screws is seated in a reduced diameter portion of the associated bone screw aperture and is spaced from a head of the bone screw.

9. The plating system for securing a first portion of bone to a second portion of bone of claim 3, wherein the first radially extending flange is generally parallel to the second radially extending flange.

10. The plating system for securing a first portion of bone to a second portion of bone of claim 3, wherein the second radially extending flange is at least partially disposed above an upper surface of the plate member.

11. A method of surgically repairing bone with an elongated plate having a plurality of bone screw apertures, the method comprising the steps of:

locating a locking ring in one of the bone screw apertures, the locking ring defining a locking ring opening and being resiliently expandable from a retracted state to an expanded state such that the locking ring opening has a first opening diameter in the retracted state and a second, larger opening diameter in the expanded state;

inserting a bone screw into the one of the bone screw apertures, the bone screw having a head with a head diameter greater than the first opening diameter and less than the second opening diameter; and removing the bone screw from the one bone screw aperture with a tool having a first portion threadably engaging the head of the bone screw and a second portion resiliently expanding the locking ring to the expanded state.

12. The method of securing a first bone portion relative to a second bone portion of claim 11; wherein the step of threadably engaging the head of the bone screw with the first portion of the tool includes the step of threadably engaging an internally threaded aperture of the head.

13. The method of securing a first bone portion relative to a second bone portion of claim 11, further comprising the step of rotating the at least one bone screw with the second portion of the tool.

14. The method of surgically repairing bone with an elongated plate having a plurality of bone screw apertures of claim 11, wherein the step of threadably engaging the head includes the step of drawing the second portion downward to resiliently expand the locking ring to the expanded state.

15. The method of surgically repairing bone with an elongated plate having a plurality of bone screw apertures of claim 11, wherein the step of inserting a bone screw into the one of the bone screw apertures includes the step of producing an audible click with the locking ring.

16. A system for surgically repairing bone, the system comprising:

an elongated plate having a plurality of bone screw apertures;

a locking ring disposed in one of the bone screw apertures, the locking ring defining a locking ring opening and being resiliently expandable from a retracted state to an expanded state such that the locking ring opening has a first opening diameter in the retracted state and a second, larger opening diameter in the expanded state;

a bone screw inserted into the one of the bone screw apertures, the bone screw having a head with a diameter greater than the first opening1 diameter and less than the second opening diameter; and a tool for removing the bone screw from the one bone screw aperture, the tool having a first portion threadably engaging the head of the bone screw and a second portion for resiliently expanding the locking ring to the expanded state.

17. The system for surgically repairing bone of claim 16, wherein the first portion of the tool threadably engages an internally threaded aperture provided in the head of the bone screw.

18. The system for surgically repairing bone of claim 16, wherein the second portion of the tool includes a hollow cylindrical member surrounding the first portion.

19. The system for surgically repairing bone of claim 18, wherein the second portion includes a tip having a plurality of drive elements for engaging a corresponding number of slots provided in the head of the bone screw.

20. The system for surgically repairing bone of claim 19, wherein the drive elements of the plurality of drive elements are radially spaced about the first portion and include outer surfaces on a circle having a diameter substantially equal to the second diameter of the locking ring.

21. The system for surgically repairing bone of claim 16, wherein the first portion is independently rotatable relative to the second drive portion.

* * * * *